(12) United States Patent
Geng et al.

(10) Patent No.: US 10,912,769 B2
(45) Date of Patent: Feb. 9, 2021

(54) 1-[(PYRIDIN-3-YL-SULFONYL)-1H-PYRROL-3-YL] METHANAMINE DERIVATIVE AND PHARMACEUTICAL COMPOSITION AND USE THEREOF

(71) Applicants: Jiangsu Jibeier Pharmaceutical Co. Ltd., Zhenjiang (CN); Zhenjiang San An Pharmaceutical Co. Ltd., Zhenjiang (CN)

(72) Inventors: Zhongyi Geng, Zhenjiang (CN); Xinghai Chen, Zhenjiang (CN)

(73) Assignees: Jiangsu Jibeier Pharmaceutical Co. Ltd., Jiangsu (CN); Zhenjiang San An Pharmaceutical Co. Ltd., Jiangsu (CN)

( * ) Notice: Subject to any disclaimer, the term of this patent is extended or adjusted under 35 U.S.C. 154(b) by 0 days.

(21) Appl. No.: 16/337,714

(22) PCT Filed: Sep. 27, 2017

(86) PCT No.: PCT/CN2017/103744
§ 371 (c)(1),
(2) Date: Mar. 28, 2019

(87) PCT Pub. No.: WO2018/059455
PCT Pub. Date: Apr. 5, 2018

(65) Prior Publication Data
US 2020/0030306 A1    Jan. 30, 2020

(30) Foreign Application Priority Data
Sep. 29, 2016 (CN) .......................... 2016 1 0870802

(51) Int. Cl.
*C07D 401/12* (2006.01)
*A61K 31/4439* (2006.01)
*A61P 1/04* (2006.01)

(52) U.S. Cl.
CPC ............ *A61K 31/4439* (2013.01); *A61P 1/04* (2018.01); *C07D 401/12* (2013.01)

(58) Field of Classification Search
CPC ...... C07D 401/12; A61K 31/4439; A61P 1/04
(Continued)

(56) References Cited

FOREIGN PATENT DOCUMENTS

| CN | 105693693 A | 6/2016 | |
|---|---|---|---|
| EP | 3 219 710 A1 | 9/2017 | |
| WO | WO-9526325 A2 * | 10/1995 | ............ C07B 59/002 |

OTHER PUBLICATIONS

Rober Wolen the application of stable Isotopes to studies of Drug bioavailibility and Bioequivalence. (Year: 1986).*

(Continued)

*Primary Examiner* — Rita J Desai
(74) *Attorney, Agent, or Firm* — Fish & Richardson P.C.

(57) ABSTRACT

Provided in the present invention are a 1-[(pyridin-3-yl-sulfonyl)-1h-pyrrol-3-yl] methanamine derivative having the structure shown below in formula (I) and a pharmaceutical composition and use thereof. The 1-[(pyridin-3-yl-sulfonyl)-1h-pyrrol-3-yl] methanamine derivative provided in the present invention has good gastric acid secretion inhibitory activities and excellent pharmacodynamic properties, while having relatively low toxicity.

(Continued)

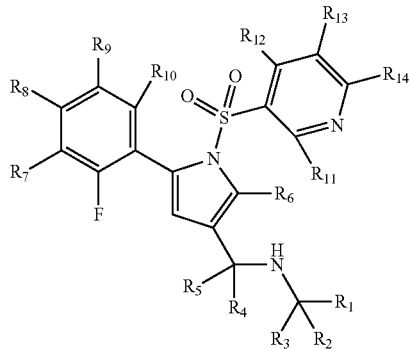

10 Claims, 1 Drawing Sheet

(58) Field of Classification Search
 USPC ..................................................... 546/276.4
 See application file for complete search history.

(56) References Cited

OTHER PUBLICATIONS

Hitomi Yamasaki et al. In vitro metabolism of TAK-438, vonoprazan fumarate, a novel potassium competitive acid blocker. (Year: 2016).*
Hori et al., "A Study Comparing the Antisecretory Effect of TAK-438, a Novel Potassium-Competitive Acid Blocker, with Lansoprazole in Animals", The Journal of Pharmacology and Experimental Therapeutics, vol. 337, No. 3, pp. 797-804, 2011.
Fisher et al., "The complexities inherent in attempts to decrease drug clearance by blocking sites of CYP-mediated metabolism", Current Opinion in Drug Discovery & Development 2006, vol. 9, No. 1, pp. 101-109.
Foster, "Deuterium Isotope Effects in the Metabolism of Drugs and Xenobiotics: Implications for Drug Design", Advances in Drug Research, vol. 14, 0-12-013314-8, pp. 1-40.
Fukuto et al., "Determination of the Mechanism of Demethylenation of (Methylenedioxy)phenyl Compounds by Cytochrome P450 Using Deuterium Isotope Effects", Journal of Medicinal Chemistry, 1991, 34, No. 9, pp. 2871-2876.
International Application No. PCT/CN2017/103744, International Search Report dated Jan. 3, 2018, 4 pp.

* cited by examiner

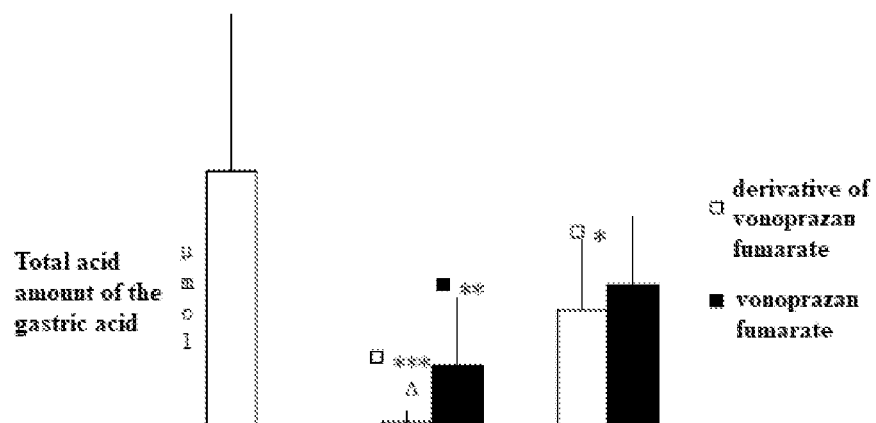

1-[(PYRIDIN-3-YL-SULFONYL)-1H-PYRROL-3-YL] METHANAMINE DERIVATIVE AND PHARMACEUTICAL COMPOSITION AND USE THEREOF

CROSS-REFERENCE TO RELATED APPLICATIONS

The present application is the U.S. National Stage under 35 U.S.C. § 371 of PCT International Application No. PCT/CN2017/103744, filed on Sep. 27, 2017, which claims the benefit of Chinese Application No. 201610870802.7 filed on Sep. 29, 2016. The foregoing are incorporated herein by reference in their entirety.

TECHNICAL FIELD

The present disclosure belongs to the field of medicine, and provides a 1-[(pyridin-3-yl-sulfonyl)-1H-pyrrol-3-yl]methanamine derivative, as well as a pharmaceutical composition or preparation comprising such compound, and use thereof in preparation of a drug for treating acid-related diseases.

BACKGROUND

Acid-related diseases (ARDs) are a class of upper gastrointestinal diseases wherein gastric acid is closely related to the pathogenesis, for example, gastro-oesophageal reflux disease (GERD), dyspepsia, gastrointestinal ulcer, gastritis, duodenitis, Zollinger-Ellison syndrome, and digestive tract diseases caused by nonsteroidal anti-inflammatory drug(s). The incidence rate of the acid-related diseases has increased year by year around the world. Clinically, the acid-related diseases are among the most common and prevalent diseases of the digestive system.

Gastric proton pump enzyme ($H^+$, $K^+$-ATPase) is the main target of the drugs treating the acid-related diseases. The two main classes of drugs which act on the gastric proton pump enzyme are potassium-competitive acid blockers (P-CABs) and proton pump inhibitors (PPIs), respectively. Among them, the proton pump inhibitors bind to the enzyme irreversibly by forming covalent complexes on specific cysteine residues, and the potassium-competitive acid blockers inhibit the secretion of gastric acid reversibly by competing with $K^+$ on the surface of lumen.

Vonoprazan is a potassium-competitive acid blocker which inhibits and terminates the secretion of gastric acid in advance by inhibiting the combination of $K^+$ to $H^+$, $K^+$-ATPase (proton pump). However, many adverse drug metabolic problems may occur during the treatment using Vonoprazan, and the resulting active metabolite(s) may cause toxicity or cause side effects to human body. Phenomena such as loose stools, diarrhea, bitterness, upper abdominal pain and macula may appear during the treatment with Vonoprazan.

The present disclosure is proposed to overcome the deficiencies in the prior art and to meet the growing needs of the patients. The present disclosure provides an improved compound showing excellent inhibitory effect on the secretion of gastric acid. As compared with other known drugs, the compound of the present disclosure may exhibit better pharmacodynamic properties and lower toxicity.

SUMMARY

Problem to be Solved

The object of the present disclosure is to provide a 1-[(pyridin-3-yl-sulfonyl)-1H-pyrrol-3-yl]methanamine derivative and use thereof; further, the present disclosure provides a 1-[(pyridin-3-yl-sulfonyl)-1H-pyrrol-3-yl]methanamine derivative having the structure represented by formula (I), pharmaceutical composition and pharmaceutical preparation thereof, and use thereof in preparation of a drug for treating acid-related diseases.

Solution to Problem

The present disclosure provides a compound having the structure represented by the following formula (I) or a derivative thereof, and the derivative is a pharmaceutically acceptable salt, prodrug, N-oxide, isomer, solvate or hydrate of the compound,

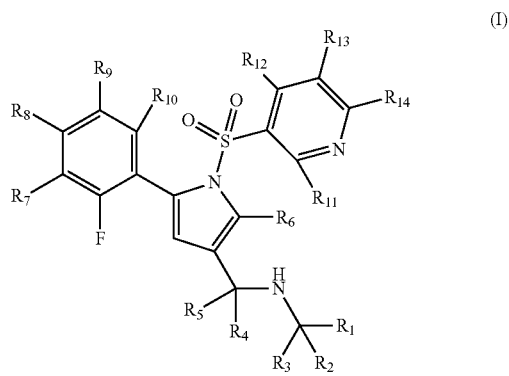

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ in formula (I) are each independently hydrogen or deuterium, provided that at least one of them is deuterium.

The compound or a derivative thereof according to the present disclosure, wherein one or more of $R_1$, $R_2$, $R_3$, $R_4$, $R_5$, $R_6$, $R_7$, $R_8$, $R_{10}$, $R_{11}$, $R_{12}$, $R_{13}$, and $R_{14}$ are deuteriums, preferably, at least two of $R_1$, $R_2$, $R_3$, $R_4$, $R_5$, $R_6$, $R_7$, $R_8$, $R_{10}$, $R_{11}$, $R_{12}$, $R_{13}$, and $R_{14}$ are deuteriums.

The compound or a derivative thereof according to the present disclosure, comprising the following compounds:
1-[5-(2-fluorophenyl)-1-(pyridin-3-yl-sulfonyl)-1H-pyrrol-3-yl]-N-methyldideuteromethanamine,
1-[5-(2-fluorophenyl)-1-(pyridin-3-yl-sulfonyl)-1H-pyrrol-3-yl]-N-trideuteromethyldideuteromethanamine,
1-[5-(2-fluorophenyl)-1-(tetradeuteropyridin-3-yl-sulfonyl)-1H-pyrrol-3-yl]-N-methyldideuteromethanamine, and
1-[5-(2-fluorophenyl)-1-(tetradeuteropyridin-3-yl-sulfonyl)-1H-pyrrol-3-yl]-N-trideuteromethyldideuteromethanamine.

The compound or a derivative thereof according to the present disclosure, wherein the pharmaceutically acceptable salt is an acid addition salt of the compound represented by formula (I), preferably a fumaric acid addition salt of the compound of formula (I).

The compound or a derivative thereof according to the present disclosure, wherein the compound or the derivative thereof is a single crystal or a polymorph.

The present disclosure also provides a pharmaceutical composition, wherein the pharmaceutical composition comprises the compound or a derivative thereof according to the present disclosure, and one or more of a pharmaceutically acceptable carrier, excipient, diluent, thickener, adjuvant, and preservative.

The composition according to the present disclosure, wherein the pharmaceutical composition also comprises other compounds, and said other compounds comprise one or more of a proton pump inhibitor, an oral antacid, a gastric antacid, a calcium channel blocker, a dopamine antagonist, a nitric oxide synthase inhibitor, and an anti-inflammatory agent.

The present disclosure also provides a pharmaceutical preparation, wherein the pharmaceutical preparation comprises the compound or a derivative thereof according to the present disclosure, and one or more of a pharmaceutically acceptable carrier, excipient, diluent, thickener, adjuvant, and preservative, preferably, the dosage form of the pharmaceutical preparation is a solid, a gel or a liquid.

The present disclosure also provides the use of the compound or a derivative thereof according to the present disclosure as a gastric acid secretion inhibitor.

The present disclosure also provides the use of the compound or a derivative thereof according to the present disclosure as a potassium-competitive gastric acid blocker.

The present disclosure also provides the use of the compound or a derivative thereof according to the present disclosure in preparation of a drug for treating an acid-related disease, preferably, the acid-related disease comprises gastrointestinal mucosal damage, *Helicobacter pylori* infection, gastro-oesophageal reflux, peptic ulcer, duodenal ulcer, oesophagitis, or gastric ulcer.

Advantageous Effect

The 1-[(pyridin-3-yl-sulfonyl)-1H-pyrrol-3-yl]methanamine derivative provided by the present disclosure has good inhibitory activity on the secretion of gastric acid and excellent pharmacodynamic properties, as well as lower toxicity.

BRIEF DESCRIPTION OF THE DRAWINGS

FIG. 1 is a schematic illustration of the influence of a derivative of vonoprazan fumarate (Compound I-1a) and vonoprazan fumarate on the basal gastric acid secretion in rats.

DETAILED DESCRIPTION

In general, the term "substitute" means that one or more hydrogen atoms in a given structure may be substituted by specific substituent(s). Unless otherwise indicated, an optional substituted group may have a substituent by which each substitutable position of the group is substituted. When more than one position in the given structural formula may be substituted by one or more substituents selected from specific groups, then each position may be substituted by the substituents identically or differently. The term "hydrogen" represents a single hydrogen atom. The term "deuterium" represents a single deuterium atom. One such atomic group is bonded to a methyl group to form a monodeuteromethyl group (—$CDH_2$), two deuterium atoms are bonded to a methyl group to form a bi-deuteromethyl group or a dideuteromethyl group (—$CD_2H$), and three deuterium atoms are bonded to a methyl group to form a trideuteromethyl group (—$CD_3$).

In the present disclosure, deuterium substitution means that one or more hydrogens in a compound or a group are substituted by deuterium, and the deuterium substitution may be mono substitution, disubstitution, poly substitution or persubstitution. The deuterium isotope content of said deuterium at a deuterated position is at least greater than the content of the natural deuterium isotope (0.015%), preferably greater than 30%, more preferably greater than 50%, more preferably greater than 75%, more preferably greater than 95%, and more preferably greater than 99%. The terms "substituted by one or more deuterium" and "monodeuterated or multideuterated" may be used interchangeably.

The term "solvate" means a physical association of the compound of the present disclosure with one or more solvent molecules. This physical association includes various degrees of ionic bonding and covalent bonding, including hydrogen bonding. In some cases, for example, when one or more solvent molecules are incorporated into the crystal lattice of a crystalline solid, the solvate may be separated. The "solvate" includes a solution phase and a separable solvate. Non-limiting examples of the solvate include alcoholate, methanolate, and the like.

The term "hydrate" is a solvate wherein the solvent molecule is $H_2O$. The preparation of a solvate is generally known. A typical non-limiting method includes dissolving the compound in a desired amount of a desired solvent (organic matter, water, or a mixture thereof) at a temperature higher than the ambient temperature, cooling the solution at a rate sufficient to form crystal, and then separating the crystal by a standard method. Analytical techniques such as infrared spectroscopy may confirm the existence of a solvent (or water) in a crystal of a solvate (or a hydrate).

The term "prodrug" means a substance which is converted in vivo to generate a compound having the structure of formula (I) or a pharmaceutically acceptable salt of this compound. Conversion may be accomplished by various mechanisms (for example, by metabolism or chemical treatment), for example, by hydrolysis in the blood.

Examples of various forms of derivatives of a prodrug may be found in the following prior art literature: "Design and Application of Prodrugs", edited by H. Bundgaard, pp. 113-191 (1991); "Pro-drugs as Novel Delivery Systems", edited by T. Higuchi and W. Stella, Vol. 14 of the A.C.S. Symposium Series, and "Bioreversible Carriers in Drug Design", edited by Edward B. Roche, American Pharmaceutical Association and Pergamon Press, 1987.

The present disclosure uses an isomer, including a stereoisomer, a geometrical isomer, a tautomer, or the like. Among them, the "stereoisomer" includes all the enantiomerically/stereomerically pure and enantiomerically/stereoisomerically enriched compounds of the present disclosure. The compound having formula (I) may have at least one asymmetric carbon atom. All the isomers include a racemic mixture. The isomer may be prepared by reacting the optically pure or optically enriched starting materials or by isolating the isomers of the compound of formula (I) using a conventional method.

Unless otherwise indicated, all pharmaceutically acceptable salts, hydrates, solvates, prodrugs, isomers, N-oxides, single crystals or polymorphs of the compound as represented by formula (I) provided by the present disclosure all belong to the scope of the present disclosure.

The present disclosure provides a compound of 1-[(pyridin-3-yl-sulfonyl)-1H-pyrrol-3-yl] methanamine or a derivative thereof, which is the compound as represented by formula (I) or a derivative thereof, said derivative is a pharmaceutically acceptable salt, prodrug, solvate or hydrate of the compound,

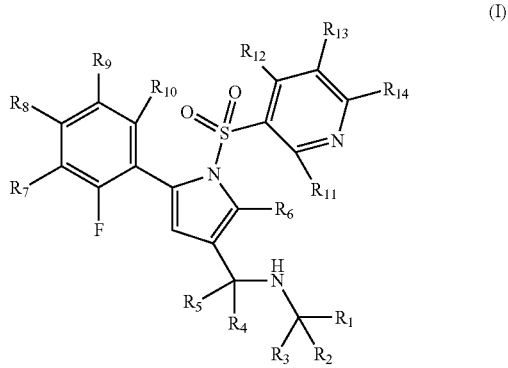

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ in formula (I) are each independently hydrogen or deuterium, provided that at least one of them is deuterium.

The above-mentioned 1-[(pyridin-3-yl-sulfonyl)-1H-pyrrol-3-yl]methanamine derivative, wherein one or more of $R_1$, $R_2$, $R_3$, $R_4$, $R_5$, $R_6$, $R_7$, $R_8$, $R_{10}$, Ru, $R_{12}$, $R_{13}$, and $R_{14}$ are deuteriums, preferably, at least two of $R_1$, $R_2$, $R_3$, $R_4$, $R_5$, $R_6$, $R_7$, $R_8$, $R_{10}$, $R_{11}$, $R_{12}$, $R_{13}$, and $R_{14}$ are deuteriums.

Preferably, the compound, the hydrate, the solvate, the prodrug, the single crystal or the polymorph of the present disclosure may be formulated as a pharmaceutically acceptable salt suitable for use as a drug. The pharmaceutically acceptable salt suitable for use as a drug refers to a salt suitable for use as a drug which is formed by the compound as represented by formula (I) provided by the present disclosure and a non-toxic acid, and said salts include inorganic salts and organic salts.

A preferred class of salt is a salt formed by the compound of the present disclosure with an acid. Acids that are suitable for forming salts include but are not limited to: inorganic acids such as hydrochloric acid, hydrobromic acid, hydrofluoric acid, sulfuric acid, nitric acid and phosphoric acid, and organic acids such as formic acid, acetic acid, propionic acid, fumaric acid, malic acid, citric acid, amygdalic acid, maleic acid, gluconic acid, oxalic acid, malonic acid, succinic acid, lactic acid, tartaric acid, picric acid, methylsulfonic acid, methylenesulfonic acid, benzene methylsulfonic acid, and benzene sulfonic acid; preferred examples of the salts with an acidic amino acid include salts with aspartic acid, glutamic acid, and the like.

Preferably, said pharmaceutically acceptable salt is the fumaric acid addition salt of the compound of formula (I).

1-[(pyridin-3-yl-sulfonyl)-1H-pyrrol-3-yl]methanamine compound represented by the above-mentioned formula (I) or a derivative thereof, said compound or the derivative thereof may be a single crystal or a polymorph.

The 1-[(pyridin-3-yl-sulfonyl)-1H-pyrrol-3-yl]methanamine derivative of the present disclosure is a preferred compound selected from the following group:

Compound 1: 1-[5-(2-fluorophenyl)-1-(pyridin-3-yl-sulfonyl)-1H-pyrrol-3-yl]-N-methyldideuteromethanamine

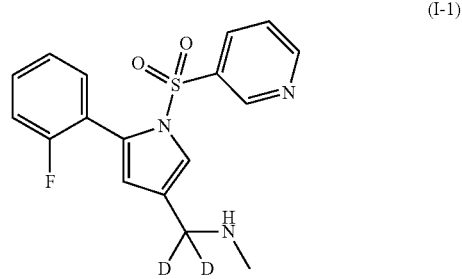 [SMILES: [2H]C([2H])(NC)c1cc(-c2ccccc2F)n(S(=O)(=O)c2cccnc2)c1]

Compound 2: 1-[5-(2-fluorophenyl)-1-(pyridin-3-yl-sulfonyl)-1H-pyrrol-3-yl]-N-trideuteromethyldideuteromethanamine

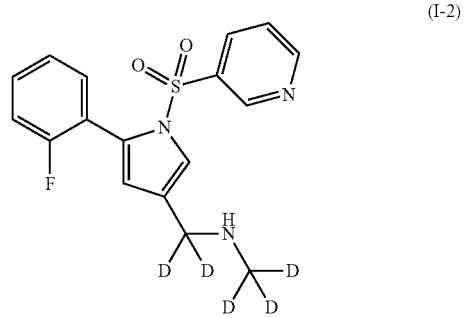 [SMILES: [2H]C([2H])([2H])NC([2H])([2H])c1cc(-c2ccccc2F)n(S(=O)(=O)c2cccnc2)c1]

Compound 3: 1-[5-(2-fluorophenyl)-1-(tetradeuteropyridin-3-yl-sulfonyl)-1H-pyrrol-3-yl]-N-methyldideuteromethanamine

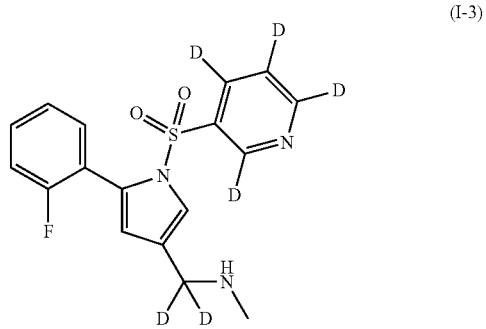 [SMILES: [2H]c1nc([2H])c(S(=O)(=O)n2cc(C([2H])([2H])NC)cc2-c2ccccc2F)c([2H])c1[2H]]

Compound 4: 1-[5-(2-fluorophenyl)-1-(tetradeutero-pyridin-3-yl-sulfonyl)-1H-pyrrol-3-yl]-N-trideuteromethyldideuteromethanamine

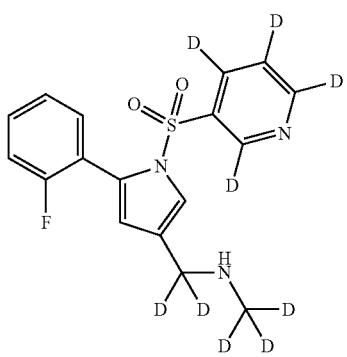

(I-4)

The compound as represented by formula (I), and each compound used in its pharmaceutically acceptable salt, solvate, hydrate, isomer, N-oxide, single crystal or polymorph may be prepared and obtained according to the preparation methods provided by the present disclosure, but is not limited to the same.

The present disclosure also provides a pharmaceutical composition, which comprises the compound according to the present disclosure or a derivative thereof, and one or more of a pharmaceutically acceptable carrier, excipient, diluent, thickener, adjuvant, and preservative.

The present disclosure also provides a pharmaceutical preparation, which comprises the compound according to the present disclosure or a derivative thereof, and one or more of a pharmaceutically acceptable carrier, excipient, diluent, thickener, adjuvant, and preservative, preferably, the dosage form of the pharmaceutical preparation is a solid, a gel or a liquid.

The pharmaceutical composition or the pharmaceutical preparation of the present disclosure may also comprise one or more of a lubricant, a binder, a disintegrant, a water-soluble polymer, a basic inorganic salt, a solvent, a dissolution assistant, a suspending agent, an isotonic agent, a buffer, a soothing agent, an antioxidant, a coloring agent, a sweetener, an acidulant, a foaming agent, and a flavoring agent.

The pharmaceutical composition of the present disclosure may be administered in the form of a tablet (including a sugar-coated tablet and a film-coated tablet), a powder, a granule, a capsule (including a soft capsule), an orally disintegrating tablet, an orally disintegrating film, a liquid, an injection, a suppository, a sustained-release preparation, an ointment, and the like.

The pharmaceutical composition and the pharmaceutical preparation of the present disclosure reduce the problem of adverse drug metabolism, and reduce toxicity and other side effects during the treatment process.

The present disclosure also provides the use of the compound or a derivative thereof according to the present disclosure as a gastric acid secretion inhibitor.

The present disclosure also provides the use of the compound or a derivative thereof according to the present disclosure as a potassium-competitive gastric acid blocker. Preferably, the drug of the present disclosure may be administered alone, or administered in combination with other pharmaceutically acceptable compounds.

Other alternative compounds include but are not limited to: (1) proton pump inhibitors, such as lansoprazole and omeprazole; (2) oral antacids, such as Maalox®; (3) mucosal protective agents, such as polaprezinc; (4) gastric antacids, such as itriglumide; (5) calcium channel blockers, such as propafenone; (6) dopamine antagonists, such as levosulpiride; and (7) nitric oxide synthase inhibitors, such as guanidinoethyl disulfide or nitroflurbiprofen.

Other alternative compounds may also include anti-inflammatory agents, said anti-inflammatory agents include one or more of acetylsalicylic acid (ASA), flurbiprofen, sodium salicylate, paracetamol, ibuprofen, ketoprofen, fentiazac, tilomisole, carprofen, suprofen, pirprofen, fenbufen, indomethacin, diclofenac, naproxen, piroxicam (feldene), tebufelone, etodolac, nabumetone, tenidap, antipyrine, aminopyrine, analgin, aminopyrone, phenylbutazone, clofezone, oxyphenbutazone, apazone, fenclofenac, benzidamine, bucolome, cinchophen, clonixin, epirizole, fenoprofen, floctafeninl, flufenamic acid, glaphenine, indoprofen, meclofenamic acid, mefenamic acid, niflumic acid, sulindac, tolmetin, alclofenac, tiaramide, proquazone, bufexamac, phenacetin, flumizole, tinoridine, timegadine, dapsone, diflunisal, benorylate, menir, oxaprozin, tiaprofenic acid, feprazone, or sudoxicam.

The present disclosure al so provides use of the above-mentioned 1-[(pyridin-3-yl-sulfonyl)-1H-pyrrol-3-yl]methanamine derivative in preparation of a drug for treating an acid-related diseases. Preferably, said acid-related disease comprises gastrointestinal mucosal damage, *Helicobacter pylori* infection, Zollinger-Ellison syndrome, gastro-oesophageal reflux, peptic ulcer, duodenal ulcer, oesophagitis, or gastric ulcer.

EXAMPLE

Hereinafter, the preparation method of the compound of the structure of formula (I) in the present disclosure is further described in detail. However, these specific methods do not constitute any limitation to the present disclosure. The compound of the present disclosure may also be prepared conveniently by optionally combining various synthetic methods described in the present specification or known in the art, and such combinations may be readily performed by those skilled in the art to which the present disclosure pertains.

The reagents and the raw materials used in the examples provided in the present disclosure and in the testing are all commercially available.

Example 1

Preparation of 1-[5-(2-fluorophenyl)-1-(pyridin-3-yl-sulfonyl)-1H-pyrrol-3-yl]-N-methyldideuteromethanamine (I-1)

Step 1: Preparation of the Intermediate 5-(2-fluorophenyl)-1H-pyrrole-3-dideuteromethanol (I-1-b)

Under the protection of argon gas, in a moisture- and oxygen-free dry flask, ethyl 5-(2-fluorophenyl)-1H-pyrrole-3-carboxylate (I-1-a) (1.0 g, 5.71 mmol) was dissolved in tetrahydrofuran (20 mL), and cooled to −78° C. A solution of lithium aluminum deuteride (0.24 g, 5.71 mmol) in tetrahydrofuran (20 mL) was added dropwise. After the mixture was reacted by stirring at a temperature of −78° C.

for 2 hours, the reaction was quenched with a solution of magnesium sulfate, and this mixture was stirred at room temperature for 0.5 hours. Ethyl acetate was added, and the organic layer was washed with a saturated saline solution, dried over anhydrous sodium sulfate, filtered and concentrated, respectively. The crude product was separated and purified by silica gel column chromatography (eluent:hexane:ethyl acetate=7:3 to 1:1) to give the intermediate 5-(2-fluorophenyl)-1H-pyrrole-3-dideuteromethanol (I-1-b).

MS (ES$^+$): m/z=194.2 (M+H)$^+$.

Step 2: Preparation of the Intermediate 5-(2-fluorophenyl)-1H-pyrrole-3-deuteroformaldehyde (I-1-c)

Under the protection of argon gas, in a moisture- and oxygen-free dry flask, 5-(2-fluorophenyl)-1H-pyrrole-3-dideuteromethanol (I-1-b) (0.75 g, 3.88 mmol) was dissolved in dichloromethane (15 mL). The mixture was stirred at room temperature and Dess-Martin periodinane (3.88 mmol, 0.3 mol dichloromethane solution) was added dropwise. The mixture was stirred at room temperature overnight. Then, a saturated sodium bicarbonate solution (15 mL) and a saturated sodium thiosulphate solution were slowly added dropwise to the reaction liquid to quench the reaction. The resulting mixture was extracted with dichloromethane (15 mL×3), and the organic phases were combined and washed with a saturated saline solution (15 mL×3). The mixture was dried over anhydrous magnesium sulfate, filtered and concentrated under reduced pressure to obtain a crude product. The crude product was separated and purified by silica gel column chromatography (eluent:hexane:ethyl acetate=4:1 to 1:1) to give 5-(2-fluorophenyl)-1H-pyrrole-3-deuteroformaldehyde (I-1-c).

LC/MS: m/z=191.2 (M+H)$^+$.

Step 3: Preparation of the Intermediate 5-(2-fluorophenyl)-1-(pyridin-3-yl-sulfonyl)-1H-pyrrole-3-deuteroformaldehyde (I-1-d)

In a dry flask, sodium hydride (60% in oil, 63.2 mg, 1.58 mmol) was washed twice with hexane and suspended in tetrahydrofuran (10 mL) in a moisture- and oxygen-free environment under the protection of argon gas. A solution of 5-(2-fluorophenyl)-1H-pyrrole-3-deuteroformaldehyde (I-1-c) (202 mg, 1.01 mmol) in tetrahydrofuran (5 mL) was added at 0° C., and the mixture was stirred at the same temperature for 30 minutes. A solution of 15-crown-5 (0.31 mL, 1.58 mmol) and pyridine-3-sulfonyl chloride (246 mg, 1.58 mmol) in tetrahydrofuran (5 mL) was added, and the mixture was stirred and reacted at room temperature for 1 hour. The reaction was monitored by thin layer chromatography (TLC), and then water was added to quench the reaction. The resulting mixture was extracted with EtOAc (10 mL×3), and the organic phases were combined and washed with a saturated sodium bicarbonate solution, water and a saturated saline solution. After dried over anhydrous sodium sulfate, the mixture was concentrated under reduced pressure to obtain a crude product. The crude product was purified by silica gel column chromatography (eluent:hexane:ethyl acetate=19:1 to 1:1) to give the intermediate 5-(2-fluorophenyl)-1-(pyridin-3-yl-sulfonyl)-1H-pyrrole-3-deuteroformaldehyde (I-1-d).

LC-MS: m/z=332.3 (M+H)$^+$.

Step 4: Preparation of 1-[5-(2-fluorophenyl)-1-(pyridin-3-yl-sulfonyl)-1H-pyrrol-3-yl]-N-methyldideuteromethanamine (I-1)

In a moisture- and oxygen-free environment and under the protection of argon gas, 5-(2-fluorophenyl)-1-(pyridin-3-yl-sulfonyl)-1H-pyrrole-3-deuteroformaldehyde (I-1-d) (100 mg, 0.3 mmol) was dissolved in dichloromethane (5 mL) in a dry flask. Under ice cooling, a solution of methanamine-N,N-d2 (17 mg, 0.45 mmol) in tetrahydrofuran (1 mL) was added dropwise, and the mixture was stirred at room temperature for 2 hours. Under ice cooling, sodium borodeuteride (0.07 g) was added in portions, and the mixture was stirred at room temperature for 1 hour. The reaction was monitored by TLC. A saturated aqueous solution of sodium bicarbonate was added to quench the reaction, and the mixture was extracted with dichloromethane. The extracted liquid was washed with a saturated saline, dried over anhydrous sodium sulfate, and concentrated. The mixture was purified by basic silica gel column chromatography (eluent: hexane:ethyl acetate=1:1; ethyl acetate:methanol=5:1) to give 1-[5-(2-fluorophenyl)-1-(pyridin-3-yl-sulfonyl)-1H-pyrrol-3-yl]-N-methyldideuteromethanamine (I-1).

LC-MS: 348.4 (M+1).

The specific reaction scheme was as follows:

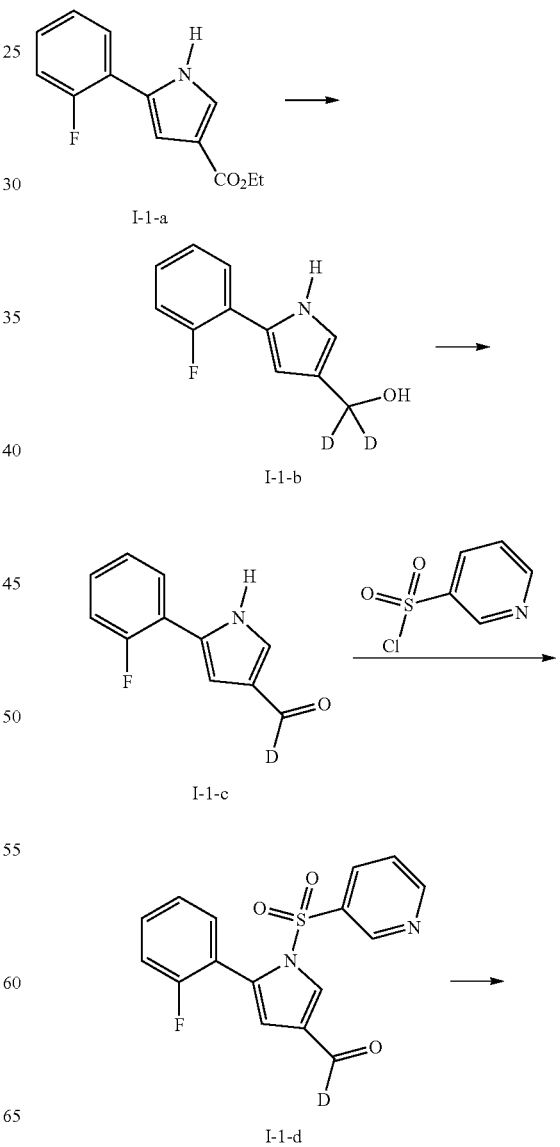

-continued

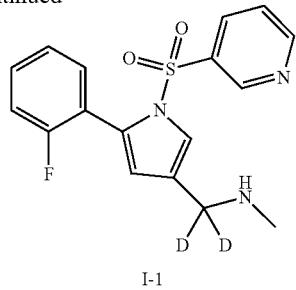

I-1

Example 2

Preparation of 1-[5-(2-fluorophenyl)-1-(pyridin-3-yl-sulfonyl)-1H-pyrrol-3-yl]-N-methyldideuteromethanamine fumarate (I-1a)

0.5 g of 1-[5-(2-fluorophenyl)-1-(pyridin-3-yl-sulfonyl)-1H-pyrrol-3-yl]-N-methyldideuteromethanamine (I-a) was dissolved in a mixed solvent of isopropanol (5 mL) and absolute ethanol (2 mL), and 0.13 g of fumaric acid was added under stirring. The mixture was then heated to 50° C., refluxed for 30 minutes, naturally cooled to room temperature under stirring, stirred for another 2 hours, filtered, and dried to give 0.45 g of 1-[5-(2-fluorophenyl)-1-(pyridin-3-yl-sulfonyl)-1H-pyrrol-3-yl]-N-methyldideuteromethanamine fumarate (I-1a).

LC-MS: 348.4 (M+1).

$^1$H-NMR (DMSO-$d_6$) δ 2.46 (s, 3H), 6.45 (s, 2H), 6.52 (s, 1H), 7.07-7.15 (m, 1H), 7.21-7.23 (m, 2H), 7.49-7.64 (m, 2H), 7.78 (d, J=1.8 Hz, 1H), 7.82-7.90 (m, 1H), 8.56-8.57 (m, 1H), 8.88-8.89 (m, 1H).

Example 3

Preparation of 1-[5-(2-fluorophenyl)-1-(pyridin-3-yl-sulfonyl)-1H-pyrrol-3-yl]-N-trideuteromethyldideuteromethanamine (I-2)

In accordance with the method of Example 1, methanamine-N,N-d2 in Example 1 was replaced with methanamine-d5 to prepare and obtain 1-[5-(2-fluorophenyl)-1-(pyridin-3-yl-sulfonyl)-1H-pyrrol-3-yl]-N-trideuteromethyldideuteromethanamine (I-2).

LC-MS: 351.4 (M+1).

Example 4

Preparation of 1-[5-(2-fluorophenyl)-1-(pyridin-3-yl-sulfonyl)-1H-pyrrol-3-yl]-N-trideuteromethyldideuteromethanamine fumarate (I-2a)

1-[5-(2-fluorophenyl)-1-(pyridin-3-yl-sulfonyl)-1H-pyrrol-3-yl]-N-trideuteromethyldideuteromethanamine fumarate (I-2a) was prepared and obtained in accordance with the method of Example 2.

LC-MS: 351.4 (M+1).

Example 5

Preparation of 1-[5-(2-fluorophenyl)-1-(tetradeuteropyridin-3-yl-sulfonyl)-1H-pyrrol-3-yl]-N-methyldideuteromethanamine (I-3)

In accordance with the method of Example 1, pyridine-3-sulfonyl chloride in Example 1 was replaced with tetradeuteropyridine-3-sulfonyl chloride to prepare and obtain 1-[5-(2-fluorophenyl)-1-(tetradeuteropyridin-3-yl-sulfonyl)-1H-pyrrol-3-yl]-N-methyldideuteromethanamine (I-3).

LC-MS: 352.4 (M+1).

Example 6

Preparation of 1-[5-(2-fluorophenyl)-1-(tetradeuteropyridin-3-yl-sulfonyl)-1H-pyrrol-3-yl]-N-methyldideuteromethanamine fumarate (I-3a)

1-[5-(2-fluorophenyl)-1-(tetradeuteropyridin-3-yl-sulfonyl)-1H-pyrrol-3-yl]-N-methyldideuteromethanamine fumarate (I-3a) was prepared and obtained in accordance with the method of Example 2.

LC-MS: 352.4 (M+1).

Example 7

Preparation of 1-[5-(2-fluorophenyl)-1-(tetradeuteropyridin-3-yl-sulfonyl)-1H-pyrrol-3-yl]-N-trideuteromethyldideuteromethanamine (I-4)

In accordance with the method of Example 1, methanamine-N,N-d2 in Example 1 was replaced with methanamine-d5, and pyridine-3-sulfonyl chloride was replaced with tetradeuteropyridine-3-sulfonyl chloride to prepare and give 1-[5-(2-fluorophenyl)-1-(tetradeuteropyridin-3-yl-sulfonyl)-1H-pyrrol-3-yl]-N-trideuteromethyldideuteromethanamine (I-4).

LC-MS: 355.5 (M+1).

Example 8

1-[5-(2-fluorophenyl)-1-(tetradeuteropyridin-3-yl-sulfonyl)-1H-pyrrol-3-yl]-N-trideuteromethyldideuteromethanamine fumarate (I-4a) was prepared and obtained in accordance with the method of Example 2.

LC-MS: 355.5 (M+1).

Example 1-B

Preparation of 1-[5-(2-fluorophenyl)-1-(pyridin-3-yl-sulfonyl)-1H-pyrrol-3-yl]-N-methyldideuteromethanamine (I-1b)

The preparation scheme was as follows:

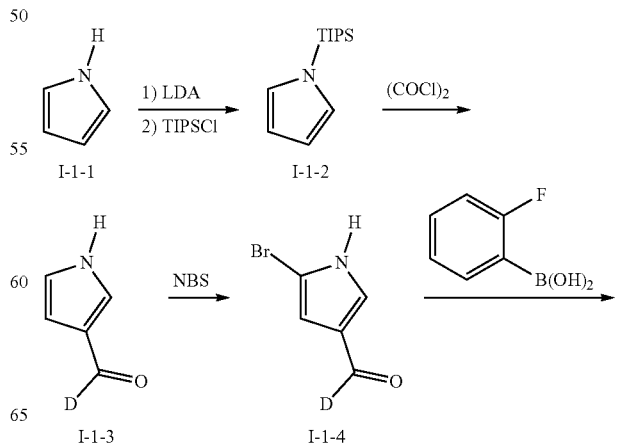

-continued

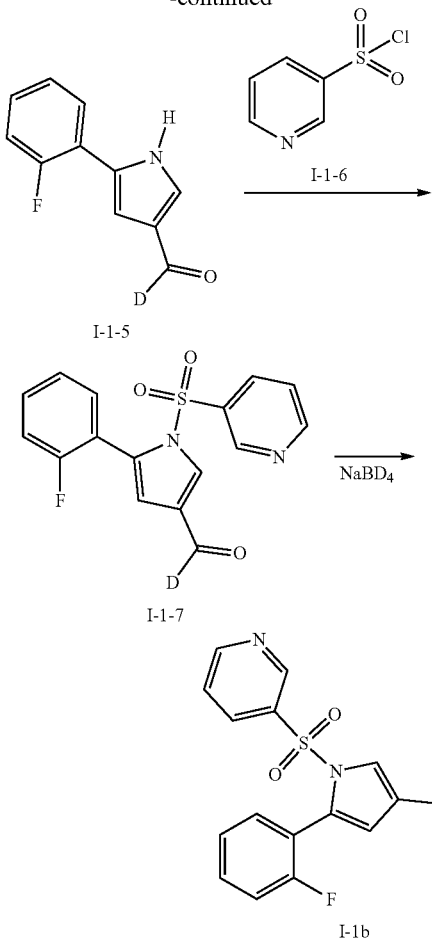

Step 1: Preparation of the Intermediate 1-triisopropylsilyl-pyrrole (Compound I-1-2)

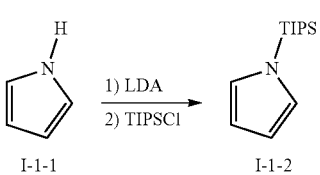

Under the protection of argon gas, 1H-pyrrole (Compound I-1-1, 17.4 g, 259 mmmol) was dissolved in 200 mL of tetrahydrofuran (THF), and the mixture was slowly added dropwise to a solution of sodium hydride (NaH, 13.7 g, 285 mmol) in THF (400 mL). The mixture was kept at 0° C. and stirred for 1.5 hours, then triisopropylchlorosilane (TIPSCl, 50 g, 259 mmol) was slowly added dropwise to the reaction system, and the mixture was allowed to stand overnight at room temperature after the completion of addition. After the completion of the reaction, the reaction mixture was poured into ice water, ethyl acetate was added, and the organic layer was washed with a saturated saline solution, dried over anhydrous sodium sulfate, filtered and concentrated, respectively. The mixture was separated and purified by silica gel column chromatography (eluent:hexane:ethyl acetate=7:3 to 1:1) to give the intermediate 1-(triisopropyl silyl)pyrrole (Compound I-1-2).

Step 2: Preparation of the Intermediate 1H-pyrrole-3-deuteroformaldehyde (Compound I-1-3)

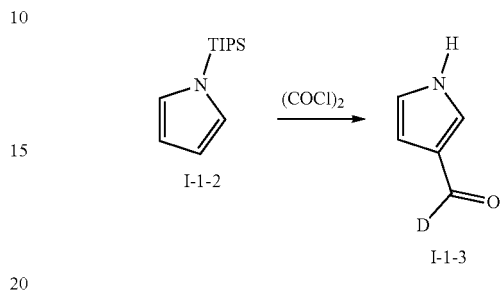

Under the protection of argon gas, a solution of 2M N,N-dimethylformamide-d7 (DMF-d₇) in dichloromethane (DCM) was added dropwise to a solution of 0.18 M of oxalyl chloride in DCM at 0° C. After the mixture was stirred at 0° C. for 30 min, Compound I-1-2 was quickly added to the reaction system, and then the mixture was refluxed at 50° C. for 30 min and the solvent was removed by vacuum. 1M NaOH solution was added, and the mixture was stirred at room temperature for 12 hours. Ethyl acetate was added, and the organic layer was washed with a saturated saline solution, dried over anhydrous sodium sulfate, filtered and concentrated, respectively. The crude product was separated and purified by silica gel column chromatography (eluent: hexane:ethyl acetate=4:1 to 1:1) to give the intermediate 1-H-pyrrole-3-deuteroformaldehyde (Compound I-1-3).

Step 3: Preparation of the Intermediate 2-bromo-1H-pyrrole-4-yl-deuteroformaldehyde (Compound I-1-4)

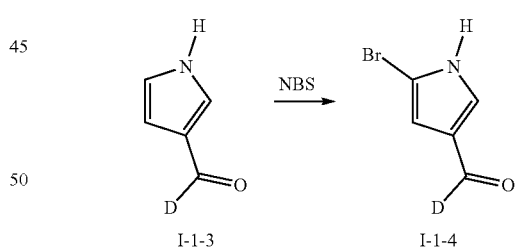

Under the protection of argon gas, the intermediate 1H-pyrrol-3-yl-deuteroformaldehyde (compound I-1-3) (250 mg) was weighed and dissolved in 3.9 mL of THF. After the mixture was cooled to −78° C., a solution of N-bromosuccinimide (NB S, 473 mg) in DMF was slowly added dropwise. After the reaction liquid was stirred at −78° C. for 1 hour, the temperature was slowly raised to −10° C. over 2 hours. The reaction liquid was poured into an ice-water system and extracted with ethyl acetate. The organic layer was washed with a saturated saline solution, dried over anhydrous sodium sulfate, filtered and concentrated, respectively. The crude product was purified by silica gel column chromatography (eluent:hexane:ethyl acetate=19:1 to 1:1) to give the intermediate 2-bromo-1H-pyrrole-4-yl-deuteroformaldehyde (Compound I-1-4).

Step 4: Preparation of the Intermediate 5-(2-fluorophenyl)-1H-pyrrol-3-yl-deuteroformaldehyde (I-1-5)

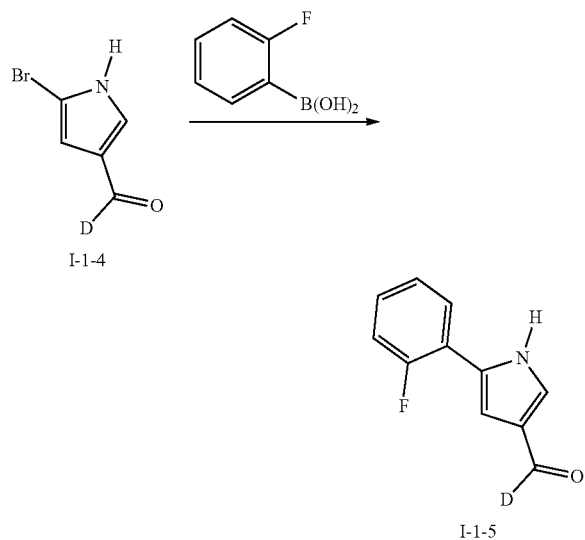

Under the protection of nitrogen gas, the intermediate 1H-2-bromo-pyrrole-4-yl-deuteroformaldehyde (Compound I-1-4) (0.57 mmol), o-fluorophenylboronic acid (0.69 mmol) and sodium carbonate (1.38 mmol) were weighed and dispersed into 5 ml of ethylene glycol dimethyl ether and 2 ml of water. After the system was sufficiently purged with nitrogen gas for three times, 0.029 mmol tetrakis (triphenylphosphine)palladium was added. After the system was sufficiently purged with nitrogen gas for three times again, the mixture was refluxed and reacted at 105° C. for 24 hours. After the completion of the reaction, the mixture was extracted with ethyl acetate, and the organic layer was respectively washed with a saturated saline solution, dried over anhydrous sodium sulfate, filtered and concentrated. The crude product was purified by silica gel column chromatography (eluent:hexane:ethyl acetate=19:1 to 1:1) to give the intermediate 5-(2-fluorophenyl)-1H-pyrrol-3-yl-deuteroformaldehyde (Compound I-1-5).

Step 5: Preparation of the Intermediate 5-(2-fluorophenyl)-1-(pyridin-3-yl-sulfonyl)-1H-pyrrol-3-yl-deuteroformaldehyde (I-1-7)

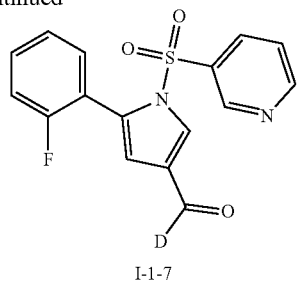

In a dry flask, sodium hydride (60% in oil, 5.9 mmol) was washed twice with hexane and suspended in tetrahydrofuran (10 mL) in a moisture- and oxygen-free environment and under the protection of argon gas. The mixture was added to a solution of 5-(2-fluorophenyl)-1H-pyrrol-3-yl-deuteroformaldehyde (Compound I-1-5) (3.9 mmol) in tetrahydrofuran (10 mL) at 0° C., and the mixture was stirred at the same temperature for 30 minutes. A solution of 15-crown-5 (1.5 mL) and pyridine-3-sulfonyl chloride (Compound I-1-6) (5.7 mmol) in tetrahydrofuran (5 mL) was added, and the mixture was stirred and reacted at room temperature for 1 hour. The reaction was monitored by a thin layer chromatography (TLC) scanner, and then water was added to quench the reaction. The resulting mixture was extracted with EtOAc (10 mL×3), and the organic phases were combined and washed with a saturated sodium bicarbonate solution, water and a saturated saline solution. After dried over anhydrous sodium sulfate, the mixture was concentrated under reduced pressure to obtain a crude product. The crude product was purified by silica gel column chromatography (eluent:hexane:ethyl acetate=19:1 to 1:1) to give the intermediate 5-(2-fluorophenyl)-1-(pyridin-3-yl-sulfonyl)-1H-pyrrol-3-yl-deuteroformaldehyde (Compound I-1-7).

Step 6: Preparation of 1-[5-(2-fluorophenyl)-1-(pyridin-3-yl-sulfonyl)-1H-pyrrol-3-yl]-N-methyldideuteromethanamine (I-1b)

In a moisture- and oxygen-free environment and under the protection of argon gas, 5-(2-fluorophenyl)-1-(pyridin-3-yl-sulfonyl)-1H-pyrrol-3-yl-deuteroformaldehyde (Compound I-1-7) (8 mmol) was dissolved in 30 mL of methanol in a dry flask. Under ice cooling, a solution of methanamine-N,N-d2 (35 mmol) in tetrahydrofuran (10 mL) was added dropwise, and the mixture was stirred at room temperature for 2 hours. Under ice cooling, sodium borodeuteride (13 mmol) was added gradually, and the mixture was stirred at room temperature for 1 hour. The reaction was monitored by TLC, and 50 mL of 1M hydrochloric acid solution was added to quench the reaction. The mixture was stirred for 5 min, the pH was adjusted to basic, and the mixture was extracted with dichloromethane. The extracted liquid was washed with a saturated saline, dried over anhydrous sodium sulfate, and concentrated. The mixture was purified by basic silica gel column chromatography (eluent:hexane:ethyl acetate=1:1; ethyl acetate:methanol=5:1) to give 1-[5-(2-fluorophenyl)-1-(pyridin-3-yl-sulfonyl)-1H-pyrrol-3-yl]-N-methyl dideuteromethanamine (I-1b).

LC-MS: 348.1 (M+1)$^+$

Example 2-b

Preparation of 1-[5-(2-fluorophenyl)-1-(pyridin-3-yl-sulfonyl)-1H-pyrrol-3-yl]-N-methyldideuteromethanamine fumarate (I-1a)

0.75 g of 1-[5-(2-fluorophenyl)-1-(pyridin-3-yl-sulfonyl)-1H-pyrrol-3-yl]-N-methyldideuteromethanamine (I-1b) was dissolved in a mixed solvent of isopropanol (5 mL) and absolute ethanol (2 mL). After a solution of 278 mg fumaric acid in 3 mL methanol was added under stirring, the mixture was heated to 50° C. and refluxed for 30 minutes, naturally cooled to room temperature under stirring, stirred for another 2 hours, filtered, and dried to give 0.45 g of 1-[5-(2-fluorophenyl)-1-(pyridin-3-yl-sulfonyl)-1H-pyrrol-3-yl]-N-methyldideuteromethanamine fumarate (I-1a).

LC-MS: 348.1 (M+1)$^+$.

$^1$H-NMR (DMSO-d$_6$) δ 2.46 (s, 3H), 6.45 (s, 2H), 6.52 (s, 1H), 7.07-7.15 (m, 1H), 7.21-7.23 (m, 2H), 7.49-7.64 (m, 2H), 7.78 (d, J=1.8 Hz, 1H), 7.82-7.90 (m, 1H), 8.56-8.57 (m, 1H), 8.88-8.89 (m, 1H).

Example 3-B

Preparation of 1-[5-(2-fluorophenyl)-1-(pyridin-3-yl-sulfonyl)-1H-pyrrol-3-yl]-N-trideuteromethyldideuteromethanamine (I-2b)

In accordance with the method of Example 1-b, methanamine-N,N-d2 in Example 1-b was replaced with methanamine-d5 to prepare and obtain 1-[5-(2-fluorophenyl)-1-(pyridin-3-yl-sulfonyl)-1H-pyrrol-3-yl]-N-trideuteromethyldideuteromethanamine (I-2b).

LC-MS: 351.4 (M+1).

Example 4-B

Preparation of 1-[5-(2-fluorophenyl)-1-(pyridin-3-yl-sulfonyl)-1H-pyrrol-3-yl]-N-trideuteromethyldideuteromethanamine fumarate (I-2a)

In accordance with the method of Example 2-b, 1-[5-(2-fluorophenyl)-1-(pyridin-3-yl-sulfonyl)-1H-pyrrol-3-yl]-N-methyldideuteromethanamine (I-1b) in Example 2-b was replaced with 1-[5-(2-fluorophenyl)-1-(pyridin-3-yl-sulfonyl)-1H-pyrrol-3-yl]-N-trideuteromethyldideuteromethanamine (I-2b) to prepare and obtain 1-[5-(2-fluorophenyl)-1-(pyridin-3-yl-sulfonyl)-1H-pyrrol-3-yl]-N-trideuteromethyldideuteromethanamine fumarate (I-2a).

LC-MS: 351.4 (M+1).

Example 5-B

Preparation of 1-[5-(2-fluorophenyl)-1-(tetradeuteropyridin-3-yl-sulfonyl)-1H-pyrrol-3-yl]-N-methyldideuteromethanamine (I-3)

In accordance with the method of Example 1-b, pyridine-3-sulfonyl chloride in Example 1-b was replaced with tetradeuteropyridine-3-sulfonyl chloride to prepare and obtain 1-[5-(2-fluorophenyl)-1-(tetradeuteropyridin-3-yl-sulfonyl)-1H-pyrrol-3-yl]-N-methyldideuteromethanamine (I-3b)

LC-MS: 352.4 (M+1).

Example 6-B

Preparation of 1-[5-(2-fluorophenyl)-1-(tetradeuteropyridin-3-yl-sulfonyl)-1H-pyrrol-3-yl]-N-methyl dideuteromethanamine fumarate (I-3a)

In accordance with the method of Example 2-b, 1-[5-(2-fluorophenyl)-1-(pyridin-3-yl-sulfonyl)-1H-pyrrol-3-yl]-N-methyldideuteromethanamine (I-1b) in Example 2-b was replaced with 1-[5-(2-fluorophenyl)-1-(tetradeuteropyridin-3-yl-sulfonyl)-1H-pyrrol-3-yl]-N-methyl dideuteromethanamine (I-3b) to prepare and obtain 1-[5-(2-fluorophenyl)-1-(tetradeuteropyridin-3-yl-sulfonyl)-1H-pyrrol-3-yl]-N-methyldi deutero methanamine fumarate (I-3a).

LC-MS: 352.4 (M+1).

Example 7-b

Preparation of 1-[5-(2-fluorophenyl)-1-(tetradeuteropyridin-3-yl-sulfonyl)-1H-pyrrol-3-yl]-N-trideuteromethyldideuteromethanamine (I-4b)

In accordance with the method described in Example 1-b, methanamine-N,N-d2 in Example 1-b was replaced with methanamine-d5, and pyridine-3-sulfonyl chloride was replaced with tetradeuteropyridine-3-sulfonyl chloride to prepare and obtain 1-[5-(2-fluorophenyl)-1-(tetradeuteropyridin-3-yl-sulfonyl)-1H-pyrrol-3-yl]-N-trideuteromethyldideuteromethanamine (I-4b).

LC-MS: 355.5 (M+1).

Example 8-b

In accordance with the method of Example 2-b, 1-[5-(2-fluorophenyl)-1-(pyridin-3-yl-sulfonyl)-1H-pyrrol-3-yl]-N-methyldideuteromethanamine (I-1b) in Example 2-b was replaced with 1-[5-(2-fluorophenyl)-1-(tetradeuteropyridin-3-yl-sulfonyl)-1H-pyrrol-3-yl]-N-trideuteromethyldideuteromethanamine (I-4b) to prepare and obtain 1-[5-(2-fluorophenyl)-1-(tetradeuteropyridin-3-yl-sulfonyl)-1-H-pyrrol-3-yl]-N-trideuteromethyldideuteromethanamine fumarate (I-4a).

LC-MS: 355.5 (M+1).

Pharmacodynamic Experiment:

An equal amount of deuterated vonoprazan fumarate derivatives I-1a, I-2a, I-3a and I-4a prepared and obtained in the Examples and vonoprazan fumarate (vonoprazan was 1-[5-(2-fluorophenyl)-1-(pyridin-3-yl-sulfonyl)-1H-pyrrol-3-yl]-N-methylmethanamine) were taken respectively and subjected to the inhibitory activity test on gastric acid secretion in rats.

SD rats which were SPF grade and weighed 180 to 200 g were selected and used in this experiment. The rats were grouped randomly with 10 rats in each group (half male and half female). Animals were fasted but free to access water for 16 hours. 1 hour after administration, the animals were anesthetized with isoflurane and fixed in a supine position. The abdomen was shaved and disinfected routinely. A 1.5 cm incision was made along the midline and below the xiphoid, the stomach was taken gently, the gastric pylorus was ligated with surgical suture at the junction of the stomach pylorus and the duodenum, and the incision was sutured. The animals were fasted and water-deprived after the surgery. After 4 hours, the animals were anesthetized by intra-abdominally injecting 1% sodium pentobarbital. The incision was opened, and the gastric cardia was ligated. The stomach was taken out and cut open along the greater curvature of stomach. The gastric juice was collected and centrifuged at 3000 rpm for 10 minutes. The supernatant was aspirated and the volume of the gastric juice was measured. 0.5 mL of the gastric juice was taken and placed in a small conical flask, a drop of phenolphthalein indicator was added, and the mixture was titrated with 0.01 mol/L sodium hydroxide until the red color appeared (the color was no longer deepened) as the endpoint. The total amount of gastric acid was calculated according to the following formula. The average secretion amount of the gastric juice and the total acid amount of the gastric juice of each administered group and the model control group were subjected to statistical tests.

$$\text{Total acid amount of the gastric juice } (\mu mol) = \frac{\text{Concentration of NaOH} \times \text{ml of NaOH}}{\text{Amount of the gastric juice taken for titration}} \times 1000 \times \text{total amount of the gastric juice}$$

$$\text{Inhibitory rate } (\%) = \frac{(\text{Total acid amount of the gastric juice of the model control group} - \text{Total acid amount of the gastric juice of the administered group})}{\text{Total acid amount of the gastric juice of the model control group}} \times 100\%$$

TABLE 1

Influence of the vonoprazan fumarate derivatives and vonoprazan fumarate on the basal gastric acid secretion in rats

| Group | Dosage (mg/kg) | Amount of gastric juice (mL) | Total acid amount of the gastric juice (μmol) | Inhibitory rate (%) ($\overline{X} \pm S$ n = 10) |
|---|---|---|---|---|
| model control group | — | 3.9 ± 1.9 | 324.0 ± 191.9 | — |
| vonoprazan fumarate derivative I-1a | 2 | 1.8 ± 0.9Δ | 15.3 ± 12.9*Δ | 95.3 |
| vonoprazan fumarate derivative I-1a | 1 | 2.6 ± 0.8 | 153.3 ± 85.9* | 52.7 |
| vonoprazan fumarate | 2 | 3.0 ± 1.3 | 84.9 ± 83.2** | 73.8 |
| vonoprazan fumarate | 1 | 3.1 ± 1.2 | 184.2 ± 83.4 | 43.1 |

As compared with the model control group,

*$P < 0.05$,

**$P < 0.01$, and

***$P < 0.001$.

As compared with the same dosage of vonoprazan fumarate,

Δ$P < 0.05$.

The inhibitory test of basal gastric acid secretion in rats was carried out after intragastric administration of the vonoprazan fumarate derivatives and vonoprazan fumarate, and the results were as shown in Table 1 and FIG. 1. The results showed that as compared with the model control group, the vonoprazan fumarate derivative (Compound I-1a) with a dosage of 2 mg/kg had a significant inhibitory effect on the secretion amount of gastric juice (P<0.01), and the vonoprazan fumarate derivative (Compound I-1a) with a dosage of 2 mg/kg and 1 mg/kg and vonoprazan fumarate with a dosage of 2 mg/kg both had significant inhibitory effect on the total acid amount of the gastric juice (P<0.05 or P<0.01). The inhibitory effects of the vonoprazan fumarate derivative (Compound I-1a) with a dosage of 2 mg/kg on the secretion amount of gastric juice and the total acid amount of the gastric juice in rats were stronger than that of the same dosage (2 mg/kg) of vonoprazan fumarate, and there was a significant difference between the two (P<0.05). As compared with vonoprazan fumarate, the vonoprazan fumarate derivatives had stronger inhibitory effect on the gastric acid secretion in rats at the same dosage.

TABLE 2

Influence of the vonoprazan fumarate derivatives and vonoprazan fumarate on the basal gastric acid secretion in rats

| Group | Dosage (mg/kg) | ($\bar{X}$ ± S n = 10) Inhibitory rate (%) |
|---|---|---|
| vonoprazan fumarate derivative I-1a | 2 | 95.3 |
| vonoprazan fumarate derivative I-2a | 2 | 95.5 |
| vonoprazan fumarate derivative I-4a | 2 | 97.4 |
| vonoprazan fumarate | 2 | 73.8 |

The results in Table 2 indicated that the intragastric administration of the vonoprazan fumarate derivatives was capable of exerting significant inhibitory effect on the basal gastric acid secretion in rats. As compared with vonoprazan fumarate, the vonoprazan fumarate derivatives had stronger inhibitory effect on the gastric acid secretion in rats at the same dosage.

Pharmacokinetic Experiment

An equal amount of Compound I-1a (1-[5-(2-fluorophenyl)-1-(pyridin-3-yl-sulfonyl)-1H-pyrrol-3-yl]-N-methyldideuteromethanamine fumarate) prepared and obtained in the Example and vonoprazan fumarate were taken respectively and subjected to a pharmacokinetic experiment.

Drug formulating manner: 16 mg of the drug (the vonoprazan fumarate derivatives or vonoprazan fumarate) was weighed and taken, and dissolved in 2 mL of N-methylpyrrolidone. 38 mL of 5% glucose injection was further added thereto to prepare a dosing solution with a concentration of 0.4 mg/mL and the dosing solution was administered by intragastric administration.

Intragastric administration: 6 SD rats (half male and half female) were taken and orally administered as a single dose (2 mg/kg). Blood samples was collected after administration, and the time points of blood collection were 0.083 hours, 0.25 hours, 0.5 hours, 1 hour, 2 hours, 3 hours, 4 hours, 6 hours, 8 hours, 12 hours, 24 hours, 36 hours, and 48 hours after the administration.

Sample collection: 200 μL of whole blood was taken at each time point of blood collection, heparin was added for anticoagulation, and the mixture was centrifuged at 12000 rpm for 5 min at 4° C. 50 μL of the plasma was taken and placed in a polypropylene tube, and the rest was used for backup and stored at −20° C. to be tested.

Plasma treatment method: To 50 μL of rat plasma anti-coagulated by heparin, 50 μL of methanol and 1004, of a solution of the internal standard etofesalamide in methanol (10 ng/mL) were added. The mixture was vortexed for 1 min and centrifuged at 12000 rpm for 10 min at 4° C. 100 μL of the supernatant was taken and placed in a vial insert, and 1 μL of the supernatant was injected for LC-MS/MS analysis.

The pharmacokinetic parameters were calculated by non-compartment model statistical moment method using Win-Nonlin 6.3 software.

TABLE 3

Pharmacokinetic parameters of rats after the 2 mg/kg intragastric administration (n = 6)

| Pharmacokinetics Parameter | Unit | TAK-438 Mean | TAK-438 SD | TAK-438d2 Mean | TAK-438d2 SD |
|---|---|---|---|---|---|
| $C_{max}$ | (ng/mL) | 67.3 | 25.8 | 74.9 | 60.8 |
| $T_{max}$ | (h) | 0.250 | 0 | 0.250 | 0 |
| $AUC_{0-6\,h}$ | (h*ng/mL) | 44.6 | 22.1 | 56.2 | 51.6 |
| $AUC_{0-\infty}$ | (h*ng/mL) | 45.0 | 21.9 | 56.4 | 51.5 |
| $t_{1/2}$ | (h) | 0.797 | 0.0801 | 0.962 | 0.153 |
| F | (%) | 33.5 | | 42.9 | |

As could be seen from the experimental data in Table 3, $AUC_{0-t}$ of 1-[5-(2-fluorophenyl)-1-(pyridin-3-yl-sulfonyl)-1H-pyrrol-3-yl]-N-methyldideuteromethanamine (TAK-438-d2) in the plasma was 56.4 h*ng/mL, and $AUC_{0-t}$ of vonoprazan (TAK-438) in the plasma was 45 h*ng/mL.

Meanwhile, it could also be seen that, as compared with vonoprazan, the absolute bioavailability of the vonoprazan derivatives prepared and obtained according to the preparation methods of the examples of the present disclosure was increased by 28.1%, $AUC_{0-t}$ was increased by 25.3%, and the time required for half of the drug to be metabolized in the body (half-life, $t_{1/2}$) was extended by 23.5%.

The above description is only illustrative of the present disclosure, and should not be understood as the limitation to the present disclosure. It can be understood that the present disclosure is not limited to the above-mentioned specific embodiments.

What is claimed is:

1. A compound having the structure represented by the following formula (I) or a pharmaceutically acceptable salt, N-oxide, solvate or hydrate thereof,

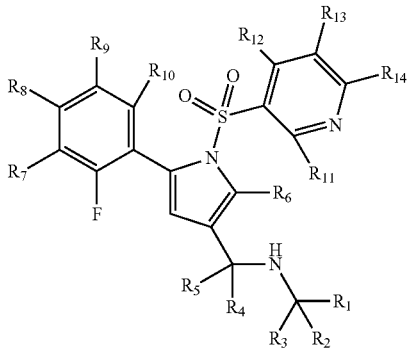

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{10}$ in formula (I) are each independently hydrogen or deuterium, provided that at least $R_4$ and $R_5$ are deuterium.

2. The compound or pharmaceutically acceptable salt, N-oxide, solvate or hydrate thereof according to claim 1, comprising the following compounds:
- 1-[5-(2-fluorophenyl)-1-(pyridin-3-yl-sulfonyl)-1H-pyrrol-3-yl]-N-methyldideuteromethanamine,
- 1-[5-(2-fluorophenyl)-1-(pyridin-3-yl-sulfonyl)-1H-pyrrol-3-yl]-N-trideuteromethyldideuteromethanamine,
- 1-[5-(2-fluorophenyl)-1-(tetradeuteropyridin-3-yl-sulfonyl)-1H-pyrrol-3-yl]-N-methyldideuteromethanamine, and
- 1-[5-(2-fluorophenyl)-1-(tetradeuteropyridin-3-yl-sulfonyl)-1H-pyrrol-3-yl]-N-trideuteromethyldideuteromethanamine.

3. The compound or pharmaceutically acceptable salt, N-oxide, solvate or hydrate thereof according to claim 1, wherein the pharmaceutically acceptable salt is an acid addition salt of the compound represented by formula (I), preferably a fumaric acid addition salt of the compound of formula (I).

4. The compound or pharmaceutically acceptable salt, N-oxide, solvate or hydrate thereof according to claim 1, wherein the compound or the pharmaceutically acceptable salt, N-oxide, solvate or hydrate thereof is a single crystal or a polymorph.

5. A pharmaceutical composition, comprising the compound or pharmaceutically acceptable salt, N-oxide, solvate or hydrate thereof according to claim 1, and one or more of a pharmaceutically acceptable carrier, excipient, diluent, thickener, adjuvant, and preservative.

6. The composition according to claim 5, wherein the pharmaceutical composition also comprises other compounds, and said other compounds comprise one or more of a proton pump inhibitor, an oral antacid, a gastric antacid, a calcium channel blocker, a dopamine antagonist, a nitric oxide synthase inhibitor, and an anti-inflammatory agent.

7. A pharmaceutical preparation, comprising the compound or pharmaceutically acceptable salt, N-oxide, solvate or hydrate thereof according to claim 1, and one or more of a pharmaceutically acceptable carrier, excipient, diluent, thickener, adjuvant, and preservative, wherein, the dosage form of the pharmaceutical preparation is a solid, a gel or a liquid.

8. A method for treating an acid-related disease, comprising administering to a subject in need thereof a therapeutically effective amount of the compound or pharmaceutically acceptable salt, N-oxide, solvate or hydrate thereof according to claim 1.

9. The method according to claim 8, wherein the acid-related disease comprises gastrointestinal mucosal damage, *Helicobacter pylori* infection, gastro-esophageal reflux, peptic ulcer, duodenal ulcer, esophagitis, or gastric ulcer.

10. A method for treating an acid-related disease, comprising administering to a subject in need thereof a therapeutically effective amount of the compound selected from:
- 1-[5-(2-fluorophenyl)-1-(pyridin-3-yl-sulfonyl)-1H-pyrrol-3-yl]-N-methyldideuteromethanamine,
- 1-[5-(2-fluorophenyl)-1-(pyridin-3-yl-sulfonyl)-1H-pyrrol-3-yl]-N-trideuteromethyldideuteromethanamine,
- 1-[5-(2-fluorophenyl)-1-(tetradeuteropyridin-3-yl-sulfonyl)-1H-pyrrol-3-yl]-N-methyldideuteromethanamine, and
- 1-[5-(2-fluorophenyl)-1-(tetradeuteropyridin-3-yl-sulfonyl)-1H-pyrrol-3-yl]-N-trideuteromethyldideuteromethanamine,
- and a pharmaceutically acceptable salt, N-oxide, solvate or hydrate thereof, wherein the acid-related disease comprises gastrointestinal mucosal damage, *Helicobacter pylori* infection, gastro-esophageal reflux, peptic ulcer, duodenal ulcer, esophagitis, or gastric ulcer.

* * * * *

UNITED STATES PATENT AND TRADEMARK OFFICE
CERTIFICATE OF CORRECTION

PATENT NO. : 10,912,769 B2
APPLICATION NO. : 16/337714
DATED : February 9, 2021
INVENTOR(S) : Zhongyi Geng and Xinghai Chen Page 1 of 1

It is certified that error appears in the above-identified patent and that said Letters Patent is hereby corrected as shown below:

On the Title Page

Column 2 (Other Publications), Line 2, Delete "bioavailibility" and insert -- bioavailability --, therefor.

Column 2 (Abstract), Line 2, Delete "-1h-pyrrol-3-yl]" and insert -- 1H-pyrrol-3-yl] --, therefor.

Column 2 (Abstract), Line 5, Delete "-1h-pyrrol-3-yl]" and insert -- 1H-pyrrol-3-yl] --, therefor.

In the Claims

Column 23, Line 19, In Claim 1, delete "$R_{10}$" and insert -- $R_{14}$ --, therefor.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*